(12) United States Patent
Richard

(10) Patent No.: US 7,217,821 B2
(45) Date of Patent: May 15, 2007

(54) PHOTOPROTECTIVE COSMETIC COMPOSITIONS COMPRISING PARA-AMINOBENZALMALONATE-SUBSTITUTED S-TRIAZINE COMPOUNDS

(75) Inventor: Hervé Richard, Villepinte (FR)

(73) Assignee: L'Oreal, Paris (FR)

( * ) Notice: Subject to any disclaimer, the term of this patent is extended or adjusted under 35 U.S.C. 154(b) by 35 days.

(21) Appl. No.: 10/829,440

(22) Filed: Apr. 22, 2004

(65) Prior Publication Data

US 2004/0234464 A1 Nov. 25, 2004

Related U.S. Application Data

(60) Provisional application No. 60/483,651, filed on Jul. 1, 2003.

(30) Foreign Application Priority Data

Apr. 22, 2003 (FR) .................. 03 04922

(51) Int. Cl.
C07D 251/70 (2006.01)
A61K 7/42 (2006.01)
A61K 31/53 (2006.01)

(52) U.S. Cl. ...................... 544/197; 514/245; 524/100; 424/59

(58) Field of Classification Search ................ 544/197; 514/245; 524/100
See application file for complete search history.

(56) References Cited

U.S. PATENT DOCUMENTS

| 5,236,698 A | 8/1993 | Richard et al. |
| 5,849,909 A | 12/1998 | Richard et al. |
| 5,928,630 A | 7/1999 | Richard et al. |

FOREIGN PATENT DOCUMENTS

| EP | 0 507 691 A | 10/1992 |
| EP | 0 790 243 A | 8/1997 |

OTHER PUBLICATIONS

French Search Report Corresponding to FR 03/04922 Issued on Oct. 17, 2003, 2 pages.

*Primary Examiner*—Venkataraman Balasubramanian
(74) *Attorney, Agent, or Firm*—Buchanan, Ingersoll & Rooney, PC

(57) ABSTRACT

Cosmetic/dermatological sunscreen compositions, suited for photoprotecting, e.g., the skin, lips, scalp and/or hair against the damaging effects of UV-radiation, contain thus effective amounts of at least one novel s-triazine compound tri-substituted with para-aminobenzalmalonate substituents.

20 Claims, No Drawings

PHOTOPROTECTIVE COSMETIC COMPOSITIONS COMPRISING PARA-AMINOBENZALMALONATE-SUBSTITUTED S-TRIAZINE COMPOUNDS

CROSS-REFERENCE TO PRIORITY/PROVISIONAL APPLICATIONS

This application claims priority under 35 U.S.C. § 119 of FR 03/04922, filed Apr. 22, 2003, and of provisional application Ser. No. 60/483,651, filed Jul. 1, 2003, both hereby expressly incorporated by reference and both assigned to the assignee hereof. This application is also a continuation of said '651 provisional.

BACKGROUND OF THE INVENTION

1. Technical Field of the Invention

The present invention relates to novel s-triazine compounds containing three particular para-aminobenzalmalonate substituents and to the cosmetic applications thereof.

This invention also relates to photoprotective cosmetic compositions comprising s-triazine compounds containing three grafted para-aminobenzalmalonate substituents as sunscreens that are active in the UV radiation range.

2. Description of Background and/or Related and/or Prior Art

It is known that radiation with wavelengths of between 280 nm and 400 nm permits tanning of the human epidermis, and that radiation with wavelengths of between 280 nm and 320 nm, known as UV-B radiation, causes skin burns and erythema which may be harmful to the development of a natural tan.

It is also known that UV-A rays, with wavelengths of between 320 nm and 400 nm, which cause tanning of the skin, are liable to induce an adverse change in the latter, especially in the case of sensitive skin and/or of skin which is continually exposed to solar radiation. UV-A rays cause, in particular, a loss of elasticity of the skin and the appearance of wrinkles, leading to premature skin aging. They promote triggering of the erythemal reaction or amplify this reaction in certain individuals and may even be the cause of phototoxic or photoallergic reactions. Thus, for aesthetic and cosmetic reasons, such as the conservation of the natural elasticity of the skin, more and more individuals wish to control the effect of UV-A rays on their skin. The term "sun protection factor" means the ratio of the irradiation time required to reach the erythema-forming threshold in the presence of the test screening agent to the irradiation time required to reach this same threshold in the absence of screening agent.

It is thus desirable to provide compounds capable of absorbing UV-A rays.

Besides their power for screening out UV-A radiation, the desired photoprotective compounds must also have good cosmetic properties, good solubility in the usual solvents and especially in fatty substances such as oils and fats, and also good resistance to water and to perspiration (remanence) and satisfactory photostability.

Among all the compounds that have been recommended for this purpose, mention may be made especially of the s-triazine derivatives bearing benzalmalonate substituents described in EP-0,507,691 by the assignee hereof. However, these compounds have a liposolubility and a photochemical stability that are still not entirely satisfactory.

SUMMARY OF THE INVENTION

A novel family of s-triazine compounds bearing three (3) unique para-aminobenzalmalonate substituents has now been developed, said novel compounds surprisingly and unexpectedly having good absorbing properties in the long UV-A radiation range, good solubility in fatty substances, good photostability and also good cosmetic qualities that are markedly improved compared with the s-triazine derivatives grafted with benzalmalonates of the prior art.

The present invention features a novel family of s-triazine compounds bearing three (3) unique para-aminobenzalmalonate substituents of formula (I), which will be more fully described hereinbelow.

This invention also features cosmetic or dermatological compositions suited for photoprotecting keratin materials, e.g., the skin, lips and hair, containing, in a cosmetically acceptable medium, at least one compound of formula (I).

Other features will become apparent from the following description.

DETAILED DESCRIPTION OF BEST MODE AND SPECIFIC/PREFERRED EMBODIMENTS OF THE INVENTION

The compounds in accordance with the present invention have the general formula (I) below:

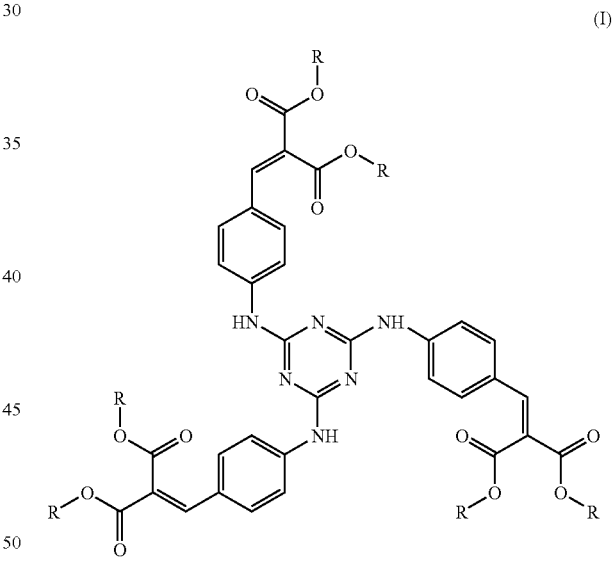

(I)

in which the radicals R, which may be identical or different, are each a radical of formula (II):

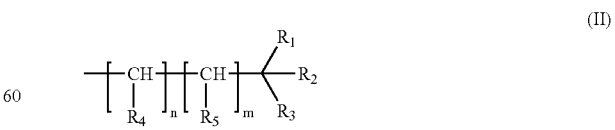

(II)

in which $R_1$ and $R_2$, which may be identical or different, are each a linear or branched $C_1$–$C_8$ alkyl radical, with the proviso that $R_1$ and $R_2$ can together form a $C_5$–$C_8$ ring member, optionally substituted with 1, 2 or 3 linear or branched $C_1$–$C_4$ alkyl radical(s); $R_3$, $R_4$ and $R_5$, which may be identical or different, are each a hydrogen atom or a linear or branched $C_1$–$C_4$ alkyl radical; n is 0 or 1; and m is 0 or 1; with the provisos that:

(i) when n=1 and $R_4$ is hydrogen, then m is equal to 0, and (ii) when $R_1$ and $R_2$ together form a $C_5$–$C_8$ ring member, then the sum n+m is other than 2.

In formula (I) above, the alkyl radicals may be selected especially from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The alkyl radical that is particularly preferred is the methyl radical.

The cycloalkyl radicals may be selected especially from among cyclopentyl, cyclohexyl and cycloheptyl radicals. The cycloalkyl radical that is particularly preferred is the cyclohexyl radical. These radicals may be substituted with $C_1$–$C_4$ alkyl radicals preferably selected from among methyl, isopropyl and tert-butyl.

Among the preferred compounds of formula (I) that will be mentioned are those for which the following two conditions are met:

(a) n=m=0 and (b) $R_1$, $R_2$ and $R_3$ are each a $C_1$–$C_4$ alkyl and more particularly methyl, or $R_3$ is hydrogen and $R_1$ and $R_2$ together form a $C_5$–$C_8$ ring member optionally substituted with one or two $C_1$–$C_4$ alkyl radicals and more particularly cyclohexyl.

Among the preferred compounds of formula (I) that will be mentioned are those for which the following two conditions are met:

(a) n=1 and $R_4$ is a $C_1$–$C_4$ alkyl, in particular methyl, or m=1 and $R_5$ is a $C_1$–$C_4$ alkyl, in particular methyl, and (b) $R_1$ and $R_2$ are each a $C_1$–$C_4$ alkyl and more particularly methyl.

Among the preferred compounds of formula (I) that are more particulary preferred, mention will be made of those selected from among the compounds of formulae (1) to (5) below:

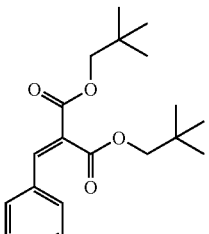

(1)

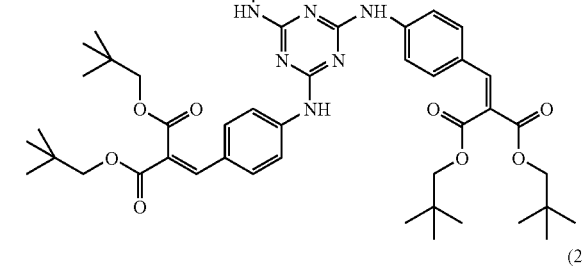

(2)

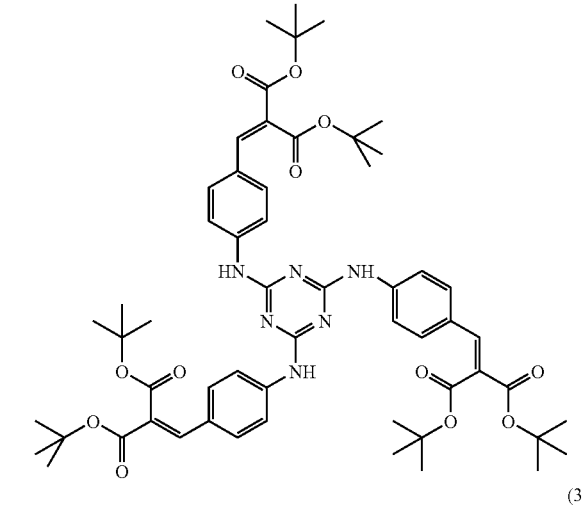

(3)

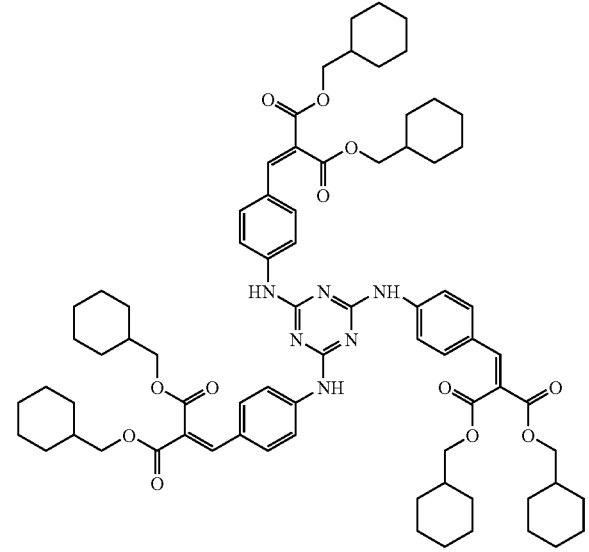

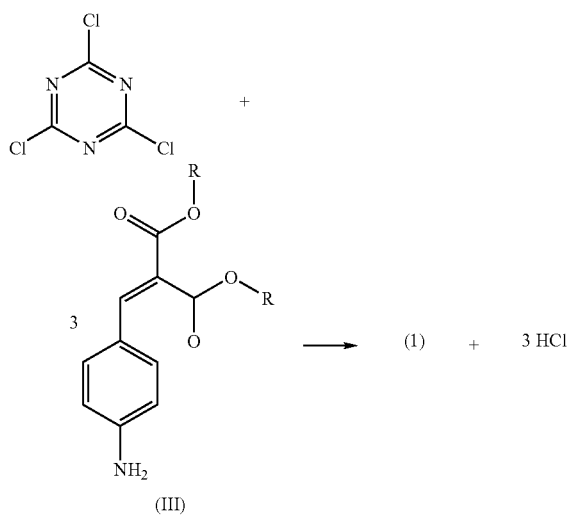

The compounds of formula (I) may be obtained according to scheme (A) below:

in which R has the definition in formula (I) above.

The above reactions may optionally be performed in the presence of a solvent (for example: toluene, xylene or acetone/water), at a temperature of between 0° C. and 250° C. and more particularly between 5° C. and 150° C.

The compounds of formula (III) may be prepared according to known methods described in FR-2,151,503 or FR-2,385,685.

The compounds of formula (I) are generally present in the composition of the invention in proportions of from 0.01% to 20% by weight and preferably from 0.1% to 10% by weight relative to the total weight of the composition.

The compositions in accordance with the invention may also comprise other additional UV-A-active and/or UV-B-active organic or mineral UV-screening agents, which are water-soluble or liposoluble, or even insoluble in the cosmetic solvents commonly used.

The additional organic screening agents are selected especially from among anthranilates; cinnamic derivatives; dibenzoylmethane derivatives; salicylic derivatives; camphor derivatives; triazine derivatives other than those of the invention such as those described in U.S. Pat. No. 4,367,390, EP-863,145, EP-517,104, EP-570,838, EP-796,851, EP-775,698, EP-878,469, EP-933,376, EP-507,691, EP-507,692, EP-790,243, EP-944,624; benzophenone derivatives; β,β-diphenylacrylate derivatives; benzotriazole derivatives; benzalmalonate derivatives other than those of the invention; benzimidazole derivatives; imidazolines; bis-benzoazolyl derivatives as described in EP-669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB-2,303,549, DE-197,26,184 and EP-893,119; benzoxazole derivatives as described in EP-0,832,642, EP-1,027,883, EP-1,300,137 and DE-101,62,844; screening polymers and screening silicones such as those described especially in WO 93/04665; dimers derived from α-alkylstyrene, such as those described in DE-198,55,649; 4,4-diarylbutadienes such as those described in EP-0,967,200, DE-197,46,654, DE-197,55,649, EP-A-1,008,586, EP-1,133,980 and EP-133,981 and mixtures thereof.

As examples of additional organic screening agents, mention may be made of those denoted herein below under their INCI names:

Para-Aminobenzoic Acid Derivatives:
PABA,
Ethyl PABA,
Ethyl dihydroxypropyl PABA,
Ethylhexyl dimethyl PABA sold in particular under the name "Escalol 507" by ISP,
Glyceryl PABA,
PEG-25 PABA sold under the name "Uvinul P25" by BASF.
  Salicylic Derivatives:
Homosalate sold under the name "Eusolex HMS" by Rona/EM Industries,
Ethylhexyl salicylate sold under the name "Neo Heliopan OS" by Haarmann and Reimer,
Dipropylene glycol salicylate sold under the name "Dipsal" by Scher,
TEA salicylate sold under the name "Neo Heliopan TS" by Haarmann and Reimer.
  Dibenzoylmethane Derivatives:
Butyl methoxydibenzoylmethane sold in particular under the trademark "Parsol 1789" by Hoffmann LaRoche,
Isopropyldibenzoylmethane.
  Cinnamic Derivatives:
Ethylhexyl methoxycinnamate sold in particular under the trademark "Parsol MCX" by Hoffmann LaRoche, Isopropyl methoxycinnamate,
Isoamyl methoxycinnamate sold under the trademark "Neo Heliopan E 1000" by Haarmann and Reimer,
Cinoxate, DEA methoxycinnamate, Diisopropyl methylcinnamate,
Glyceryl ethylhexanoate dimethoxycinnamate.
β,β-Diphenylacrylate Derivatives:
Octocrylene sold in particular under the trademark "Uvinul N539" by BASF,
Etocrylene sold in particular under the trademark "Uvinul N35" by BASF.
Benzophenone Derivatives:
Benzophenone-1 sold under the trademark "Uvinul 400" by BASF,
Benzophenone-2 sold under the trademark "Uvinul D50" by BASF,
Benzophenone-3 or Oxybenzone sold under the trademark "Uvinul M40" by BASF,
Benzophenone-4 sold under the trademark "Uvinul MS40" by BASF,
Benzophenone-5,
Benzophenone-6 sold under the trademark "Helisorb 11" by Norquay,
Benzophenone-8 sold under the trademark "Spectra-Sorb UV-24" by American Cyanamid,
Benzophenone-9 sold under the trademark "Uvinul DS-49" by BASF,
Benzophenone-12,
n-Hexyl 2-(4-diethylamino-2-hydroxybenzoyl)benzoate.
Benzylidenecamphor Derivatives:
3-Benzylidenecamphor manufactured under the name "Mexoryl SD" by Chimex,
4-Methylbenzylidenecamphor sold under the name "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.
Phenylbenzimidazole Derivatives:
Phenylbenzimidazolesulfonic acid sold in particular under the trademark "Eusolex 232" by Merck,
Disodium phenyl dibenzimidazole tetrasulfonate sold under the trademark "Neo Heliopan AP" by Haarmann and Reimer.
Triazine Derivatives:
Anisotriazine sold under the trademark "Tinosorb S" by Ciba Geigy,
Ethylhexyltriazone sold in particular under the trademark "Uvinul T150" by BASF,
Diethylhexylbutamidotriazone sold under the trademark "Uvasorb HEB" by Sigma 3V.
Phenylbenzotriazole Derivatives:
Drometrizole trisiloxane sold under the name "Silatrizole" by Rhodia Chimie,
Methylenebis(benzotriazolyl)tetramethylbutylphenol sold in solid form under the trademark "Mixxim BB/100" by Fairmount Chemical, or in micronized form as an aqueous dispersion under the trademark "Tinosorb M" by Ciba Specialty Chemicals.
Anthranilic Derivatives:
Menthyl anthranilate sold under the trademark "Neo Heliopan MA" by Haarmann and Reimer.
Imidazoline Derivatives:
Ethylhexyldimethoxybenzylidenedioxoimidazoline propionate.
Benzalmalonate Derivatives:
Polyorganosiloxanes containing benzalmalonate functions, such as Polysilicone-15 sold under the trademark "Parsol SLX" by Hoffmann LaRoche
4,4-Diarylbutadiene Derivatives:
1,1-Dicarboxy(2,2'-dimethylpropyl)-4,4-diphenylbutadiene.
Benzoxazole Derivatives:
2,4-Bis[5-1(dimethylpropyl)benzoxazol-2-yl(4-phenyl)imino]-6-(2-ethylhexyl)imino-1,3,5-triazine sold under the name Uvasorb K2A by Sigma 3V,
and mixtures thereof.

The additional organic UV-screening agents that are preferred are selected from among:
Ethylhexyl salicylate,
Ethylhexyl methoxycinnamate,
Butyl methoxydibenzoylmethane,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Anisotriazine,
Ethylhexyltriazone,
Diethylhexylbutamidotriazone,
Methylenebis(benzotriazolyl)tetramethylbutylphenol,
Drometrizole trisiloxane,
Polysilicone-15
1,1-Dicarboxy(2,2'-dimethylpropyl)-4,4-diphenylbutadiene,
2,4-Bis[5-1 (dimethylpropyl)benzoxazol-2-yl(4-phenyl)imino]-6-(2-ethylhexyl)imino-1,3,5-triazine,
and mixtures thereof.

The mineral screening agents are selected from among pigments or even nanopigments (mean size of the primary particles: generally between 5 nm and 100 nm and preferably between 10 nm and 50 nm) of coated or uncoated metal oxides such as, for example, nanopigments of titanium oxide (amorphous or crystallized in rutile and/or anatase form), of iron oxide, of zinc oxide, of zirconium oxide or of cerium oxide and mixtures thereof which are all UV photoprotective agents that are well known per se. Standard coating agents are, moreover, alumina and/or aluminum stearate. Such coated or uncoated metal oxide nanopigments are described in particular in EP-518,772 and EP-518,773.

The additional UV-screening agents in accordance with the invention are generally present in the compositions according to the invention in proportions ranging from 0.01% to 20% by weight relative to the total weight of the composition, and preferably ranging from 0.1% to 10% by weight relative to the total weight of the composition.

The cosmetic compositions according to the invention may also contain agents for artificially tanning and/or browning the skin (self-tanning agents) such as dihydroxyacetone (DHA).

The compositions in accordance with the present invention may also comprise standard cosmetic adjuvants selected especially from fatty substances, organic solvents, ionic or nonionic thickeners, softeners, humectants, antioxidants, moisturizers, desquamating agents, free-radical scavengers, antipollution agents, antibacterial agents, anti-inflammatory agents, depigmenting agents, propigmenting agents, opacifiers, stabilizers, emollients, silicones, antifoams, insect repellents, fragrances, preservatives, anionic, cationic, non-ionic, zwitterionic or amphoteric surfactants, substance P antagonists, substance CGRP antagonists, fillers, pigments, colorants, polymers, propellants, acidifying or basifying agents, or any other ingredient usually used in cosmetics and/or dermatology.

The fatty substances may be an oil or a wax or mixtures thereof. The term "oil" means a compound that is liquid at room temperature. The term "wax" means a compound that is solid or substantially solid at room temperature, and whose melting point is generally above 35° C.

Among the oils that can together form part of the composition of the fatty phase, mention may be made especially of:

mineral oils such as liquid paraffin and liquid petroleum jelly, oils of animal origin such as perhydrosqualene, oils of plant origin such as sweet almond oil, avocado oil, castor oil, olive oil, jojoba oil, sesame seed oil, groundnut oil, grapeseed oil, rapeseed oil, coconut oil, hazelnut oil, shea butter, palm oil, apricot kernel oil, beauty-leaf oil, rice bran oil, maize germ oil, wheatgerm oil, soybean oil, sunflower oil, evening primrose oil, safflower oil, passionflower oil and rye oil, synthetic oils such as purcellin oil, esters, for instance butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and esters derived from lanolic acid, such as isopropyl lanolate and isocetyl lanolate, isoparaffins and poly-α-olefins.

As other oils that may be used in the compositions according to the invention, mention may also be made of $C_{12}-C_5$ fatty alkyl benzoates (Finsolv Tenn. from Finetex), ethers, lipophilic derivatives of amino acid such as isopropyl N-lauroylsarcosinate (Eldew SL-205 from Ajinomoto), fatty alcohols such as lauryl alcohol, cetyl alcohol, myristyl alcohol, stearyl alcohol, palmityl alcohol, oleyl alcohol and 2-octyldodecanol, acetyl glycerides, octanoates and decanoates of alcohols and of polyalcohols, such as those of glycol and of glycerol, ricinoleates of alcohols and of polyalcohols such as cetyl ricinoleate, fatty acid triglycerides such as caprylic/capric triglycerides, triglycerides of $C_{10}-C_{18}$ saturated fatty acids, fluoro oils, perfluoro oils, lanolin, hydrogenated lanolin, acetylated lanolin and, finally, volatile or non-volatile silicone oils.

Needless to say, the fatty phase may also contain one or more standard lipophilic cosmetic adjuvants, for instance waxes, lipophilic gelling agents, surfactants or organic or mineral particles, and especially those that are commonly employed in the manufacture and production of antisun (sunscreen) cosmetic compositions.

Waxy compounds that may be mentioned include paraffin, carnauba wax, beeswax and hydrogenated castor oil.

Among the organic solvents that may be mentioned are lower alcohols and polyols. These lower polyols may be selected from among glycols and glycol ethers, for instance ethylene glycol, propylene glycol, butylene glycol, dipropylene glycol or diethylene glycol.

The thickeners may be selected especially from crosslinked acrylic polymers, for instance Carbomers, acrylate/$C_{10}-C_{30}$ alkylacrylate crosslinked polymers of the type such as Pemulen or polyacrylate-3 sold under the name Viscophobe DB 1000 by Amerchol; polyacrylamides such as the emulsion polyacrylamide, $C_{13}-C_{14}$ isoparaffin and laureth-7 sold under the name Sepigel 305 by SEPPIC, AMPS homopolymers or copolymers such as Hostacerin AMPS sold by Clariant, modified or unmodified guar gums and celluloses, such as hydroxy-propylated guar gum, methylhydroxyethylcellulose and hydroxypropylmethyl cellulose, xanthan gum, and nanometric silicas of the Aerosil type.

Needless to say, one skilled in this art will take care to select the optional additional compound(s) mentioned above and/or the amounts thereof such that the advantageous properties intrinsically associated with the compounds in accordance with the invention are not, or are not substantially, adversely affected by the envisaged addition(s).

The compositions according to the invention may be prepared according to techniques that are well known to those skilled in the art, in particular those intended for the preparation of emulsions of oil-in-water or water-in-oil type.

This composition may be in particular in the form of a simple or complex emulsion (O/W, W/O, O/W/O or W/O/W emulsion) such as a cream or a milk, in the form of a gel or a cream-gel, or in the form of a lotion, an oil, a powder or a solid tube, and may optionally be packaged as an aerosol and may be in the form of a mousse or a spray.

The compositions according to the invention are preferably in the form of an oil-in-water or water-in-oil emulsion.

When it is an emulsion, the aqueous phase of this emulsion may comprise a nonionic vesicular dispersion prepared according to known processes (Bangham, Standish and Watkins, J. Mol. Biol., 13, 238 (1965), FR-2,315,991 and FR-2,416,008).

When the cosmetic composition according to the invention is used to care for the human epidermis, it may be in the form of a suspension or a dispersion in solvents or fatty substances, in the form of a nonionic vesicular dispersion or in the form of an emulsion, preferably of oil-in-water type, such as a cream or a milk, or in the form of an ointment, a gel, a cream-gel, an antisun oil, a solid tube, a powder, an aerosol mousse or a spray.

When the cosmetic composition according to the invention is used for haircare, it may be in the form of a shampoo, a lotion, a gel, an emulsion or a nonionic vesicular dispersion and may constitute, for example, a rinse-out composition, to be applied before or after shampooing, before or after dyeing or bleaching, or before, during or after permanent-waving or relaxing the hair, a styling or treating lotion or gel, a blow-drying or hairsetting lotion or gel, or a composition for permanent-waving, relaxing, dyeing or bleaching the hair.

When the composition is used as a makeup product for the nails, the lips, the eyelashes, the eyebrows or the skin, such as an epidermal treatment cream, a foundation, a tube of lipstick, an eyeshadow, a makeup rouge, a mascara or an eyeliner, it may be in solid or pasty, anhydrous or aqueous form, such as oil-in-water or water-in-oil emulsions, nonionic vesicular dispersions or suspensions.

As a guide, for the antisun formulations in accordance with the invention which contain a support of oil-in-water emulsion type, the aqueous phase (especially comprising the hydrophilic screening agents) generally represents from 50% to 95% by weight and preferably from 70% to 90% by weight relative to the total weight of the formulation, the oily phase (especially comprising the lipophilic screening agents) generally represents from 5% to 50% by weight and preferably from 10% to 30% by weight relative to the total weight of the formulation, and the (co)-emulsifier(s) generally represent(s) from 0.5% to 20% by weight and preferably from 2% to 10% by weight relative to the total weight of the formulation.

The compositions according to the invention may be in the form of vaporizable fluid lotions and may be applied to the skin or the hair in the form of fine particles by means of pressurization devices. The devices in accordance with the invention are well known to those skilled in the art and comprise non-aerosol pumps or "atomizers", aerosol containers comprising a propellant and also aerosol pumps using compressed air as propellant. These devices are described in U.S. Pat. Nos. 4,077,441 and 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

This invention also features the use of a compound of formula (I) as defined above in a cosmetic or dermatological composition as an agent for screening out UV radiation.

The present invention also features the use of a compound of formula (I) as defined above in a cosmetic composition as an agent for controlling the variation in color of the skin caused by UV radiation.

Too, this invention features the use of a compound of formula (I) as defined above as a photostabilizer for synthetic polymers such as plastics or glasses, in particular spectacle glasses or contact lenses.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Preparation of 2,4,6-tris(dineopentyl 4'-aminobenzalmalonate)-s-triazine

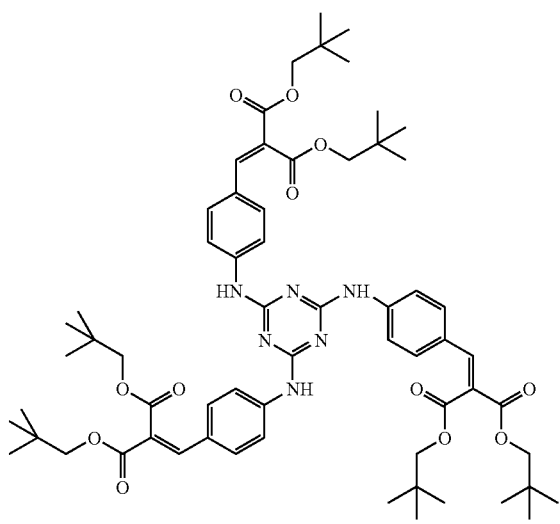

First Step: Preparation of dineopentyl malonate:

Malonic acid (40 g, 0.38 mol) and neopentyl alcohol (77.5 g, 0.88 mol) are refluxed for 3 hours in 110 ml of toluene in the presence of 0.2 ml of concentrated sulfuric acid in a reactor equipped with Dean-Stark apparatus. The water formed is removed azeotropically. The organic phase is washed 3 times with water and dried over sodium sulfate. After filtration and evaporation of the solvent under vacuum, 88 g (94% yield) of dineopentyl malonate are obtained in the form of a colorless oil, and are used in the next step without further purification.

Second Step: Preparation of dineopentyl 4-nitrobenzalmalonate:

p-Nitrobenzaldehyde (49.5 g, 0.33 mol) and dineopentyl malonate (80 g, 0.33 mol) are placed in 200 ml of toluene in a round-bottomed flask equipped with Dean-Stark apparatus, fitted with a condenser and while sparging with nitrogen. The catalyst prepared beforehand, acetic acid (2 ml) and piperidine (3.3 ml) suspended in 2 ml of toluene are added thereto. The mixture is stirred at reflux for 5 hours and the water formed is removed via the Dean-Stark apparatus. Two additions of the same amounts of catalyst were necessary.

The cooled reaction mixture is poured into water and extracted with dichloromethane. The organic phase is washed with water and then dried and concentrated under reduced pressure to a volume of 150 ml. 50 ml of isopropanol are added thereto and the product is left to crystallize. The solid obtained is filtered off and recrystallized from isopropanol. 68 g (58% yield) of dineopentyl 4-nitrobenzalmalonate are thus obtained in the form of light beige crystals, and are used in the next step without further purification.

Third Step: Preparation of dineopentyl 4-aminobenzalmalonate:

The derivative from the preceding step (67 g, 0.178 mol) is dispersed in 80 ml of acetic acid with stirring and while sparging with nitrogen. 120 ml of water are added thereto. The mixture is heated to 50° C. Iron (107 g) is added thereto portionwise without exceeding a temperature of 55° C. (introduction time: 1 hour). Acetic acid (120 ml) is then added dropwise without exceeding a temperature of 55° C. (introduction time: 2 hours). The mixture is heated for a further 4 hours at 55° C. The resulting mixture is cooled, water is added and this mixture is extracted with dichloromethane. The organic phase is washed with water, with saturated sodium bicarbonate solution and with water, and is then dried over sodium sulfate. After concentrating under reduced pressure, a yellow solid is obtained. It is recrystallized from a mixture of heptane and 1,2-dichloroethane. 43 g (69% yield) of dineopentyl 4-aminobenzalmalonate are thus obtained in the form of fibrous yellow crystals and are used in the next step without further purification.

Fourth Step: Preparation of the Derivative of Example 1:

The above derivative (42 g, 0.12 mol) is dispersed in 600 ml of toluene while sparging with nitrogen. The mixture is brought to 70° C. and a solution of cyanuryl chloride (7.5 g, 0.04 mol) in 100 ml of toluene is added dropwise. The mixture is then heated at 90° C. for 2 hours while degassing with nitrogen. After cooling, the organic phase is washed with water and then with aqueous sodium bicarbonate solution. It is concentrated under reduced pressure. The residue obtained is dissolved in a 98/2 1,2-dichloroethane/isopropanol mixture. After rapid filtration through a bed of silica, evaporation of the solvents and drying, 43 g (97% yield) of the derivative of Example 1 are obtained in the form of an amorphous pale-yellow powder:

m.p.: 95–150° C., UV (ethanol) $\lambda_{max}$=356 nm; $\epsilon_{max}$=109 810; $E_{1\%}$=956.

EXAMPLE 2

Preparation of 2,4,6-tris(bis(1,3-dimethylbutyl) 4'-aminobenzalmalonate)-s-triazine:

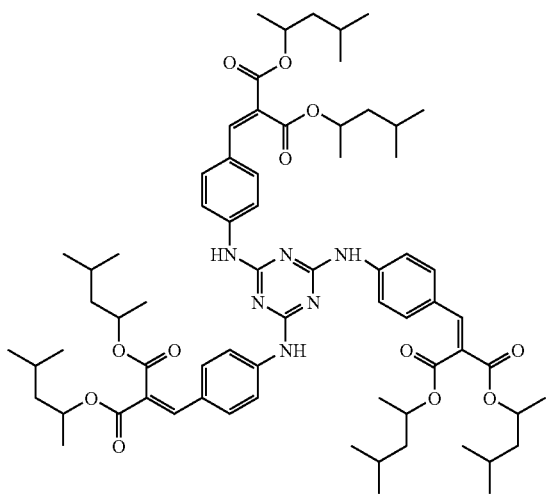

First Step: Preparation of bis(1,3-dimethylbutyl) malonate:

Malonic acid (72.8 g, 0.7 mol) and 2-methyl-4-pentanol (286 g, 2.8 mol) in 200 ml of toluene are refluxed for 2 hours in the presence of 1.8 ml of concentrated sulfuric acid in a reactor equipped with Dean-Stark apparatus. The water formed is removed azeotropically. The organic phase is washed three times with water and dried over sodium sulfate. This solution is filtered and the solvent is evaporated off. The product obtained distils at 147° C. under 20 hPa. 160 g (79% yield) of bis(1,3-dimethylbutyl) malonate are obtained in the form of a colorless oil, which is used in the next step without further purification.

Second Step: Preparation of bis(1,3-dimethylbutyl) 4-nitrobenzalmalonate:

p-Nitrobenzaldehyde (49.9 g, 0.33 mol) and bis(1,3-dimethylbutyl) malonate (90 g, 0.33 mol) are placed in 150 ml of toluene in a round-bottomed flask equipped with Dean-Stark apparatus, fitted with a condenser and while sparging with nitrogen. The catalyst prepared beforehand, acetic acid (1.9 ml) and piperidine (3.3 ml) suspended in 4 ml of toluene are added thereto. The mixture is stirred at reflux for 7 hours 30 minutes and the water formed is removed by means of the Dean-Stark apparatus. Two additions of the same amount of catalyst were necessary. The cooled reaction mixture is poured into water and extracted with dichloromethane. The organic phase is washed with water and then dried and concentrated under reduced pressure. The red-brown oil obtained is chromatographed on a column of silica (eluent: 97/3 heptane/EtOAc). 56.8 g (43% yield) of clean fractions of 1,3-dimethylbutyl 4-nitrobenzalmalonate are recovered in the form of a yellow oil and are used in the next step without further purification.

Third Step: Preparation of 1,3-dimethylbutyl 4-aminobenzalmalonate

The derivative from the preceding step (56.8 g, 0.14 mol) is dispersed in 80 ml of acetic acid with stirring and while sparging with nitrogen. 115 ml of water are added thereto. The mixture is heated to 50° C. Iron (78.2 g, 1.4 mol) is added thereto portionwise without exceeding a temperature of 55° C. (introduction time: 1 hour). Acetic acid (115 ml) is then added dropwise without exceeding a temperature of 55° C. (introduction time: 2 hours). The mixture is heated for a further 1 hour at 55° C. It is cooled, water is added and this mixture is extracted twice with dichloromethane. The organic phase is washed with water, with saturated sodium bicarbonate solution and with water, and is then dried over sodium sulfate. After concentration under reduced pressure, a red-brown oil is obtained, which is purified by passing it through a column of silica (eluent: 85/15 heptane/EtOAc). It is recrystallized from a mixture of heptane and 1,2-dichloroethane. 22.5 g (43% yield) of clean fractions of 1,3-dimethylbutyl 4-aminobenzalmalonate are recovered in the form of an orange oil, and are used in the next step without further purification.

Fourth Step: Preparation of the Derivative of Example 2:

Cyanuryl chloride (2.6 g, 0.0141 mol) is dispersed at 0° C. in 20 ml of xylene. A solution of the above derivative (15.9 g, 0.0423 mol) in 120 ml of xylene is added dropwise while sparging with nitrogen. The mixture is maintained at the reflux point of the xylene for 18 hours. After cooling, the organic phase is washed with water. The organic phase is concentrated under vacuum. The residue is taken up in dichloromethane. The organic phase is washed with aqueous sodium bicarbonate solution and then with water. It is concentrated under reduced pressure. The residue consisting of the di- and trisubstituted derivatives is subjected to a separation on a column of silica (eluent: 90/10 heptane/EtOAc).

7.83 g (46% yield) of clean fractions of the derivative of Example 2 are recovered in the form of an amorphous pale yellow powder:

m.p.: 80–140° C., UV (ethanol) $\lambda_{max}$=353 nm; $\epsilon_{max}$=110 780; $E_{1\%}$=922.

Example of Formulation in an O/W Emulsion

| Ingredients | Composition (% by weight) |
| --- | --- |
| Glyceryl monostearate/polyethylene glycol stearate 100 EO mixture (Simulsol 165 - SEPPIC) | 1 |
| Stearic acid (Stearine TP 1200 Pastilles - Stearinerie Dubois) | 1.5 |
| Polydimethylsiloxane (200 Fluid 350 CS - Dow Corning) | 0.5 |
| Cetyl alcohol (Lanette 16 NF - Cognis) | 0.5 |
| Cetylstearyl glucoside/cetylstearyl alcohol mixture (Montanov 68 - SEPPIC) | 2 |
| Triethanolamine | 0.45 |
| Capric/caprylic acid triglyceride (Myritol 317 - Cognis) | 10 |
| Compound of Example 1 | 5 |
| Glycerol | |
| Xanthan gum (Keltrol T - CP Kelco) | 0.1 |
| Acrylic acid/($C_{10}$/$C_{30}$)alkyl acrylates crosslinked copolymer (Pemulen TR-1 - Noveon) | 0.12 |
| Preservative | 1 |
| Triethanolamine | qs pH |
| Demineralized water | qs 100 g |

Compared photostabilities between a compound of the prior art and the compound according to the invention of Example 1:

Test Products:

2,4,6-tris(Diisobutyl 4'-aminobenzalmalonate)-s-triazine=prior art (Example 1 of patent EP 507 691).

2,4,6-tris(Dineopentyl 4'-aminobenzalmalonate)-s-triazine=Example 1 according to the invention.

The two products were dissolved at 5% by weight in Miglyol 812 oil. About 10 mg of oily solution are spread over 10 cm² onto the surface of a frosted-glass hollow disc; the amount is determined by weighing.

The films of oily solutions are irradiated for one hour using an Oriel sun simulator (UVA=14.2 mW/cm²; UVB=0.41 mW/cm²), and then extracted with 10 ml of ethanol containing 10% isopropanol and treated with ultrasound for 5 minutes. The quantifications of the products are performed by HPLC of the extracts.

HPLC conditions: column: UP5WOD-25QS, 250*4.6 mm, 5 μm, Interchrom; eluent: methanol (Comparative Example 1) and 96% methanol+4% water (Example 1); flow rate: 1 ml/minute; injected volume: 10 μl; detection: diode array; rt (minutes): 5.2 (Comparative Example 1) and 14.9 (Example 1).

The degrees of loss are determined by comparison of the amounts of product present in the irradiated samples and in the non-irradiated controls prepared simultaneously and treated in the same manner (average of 3 samples; S=surface area/mg solution): % loss=100*(S0-Sirr)/S0

Photostability Results

| Compounds | Test | % disappearance |
|---|---|---|
| Compound (prior art) | 1 | 11 |
| Compound (prior art) | 2 | 10 |
| Compound (prior art) | 3 | 9 |
| Example 1 | 4 | 3 |
| Example 1 | 5 | 5 |
| Example 1 | 6 | 4 |

Compound of the prior art: the loss in Miglyol is between 9% to 11% after 1 hour of exposure of a 1 mg/cm² film of 5% solution to the simulator. Example 1: the loss in Miglyol is between 3% to 5% after one hour of exposure of a 1 mg/cm² film of 5% solution to the simulator.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

The invention claimed is:

1. A compound having the following formula (I):

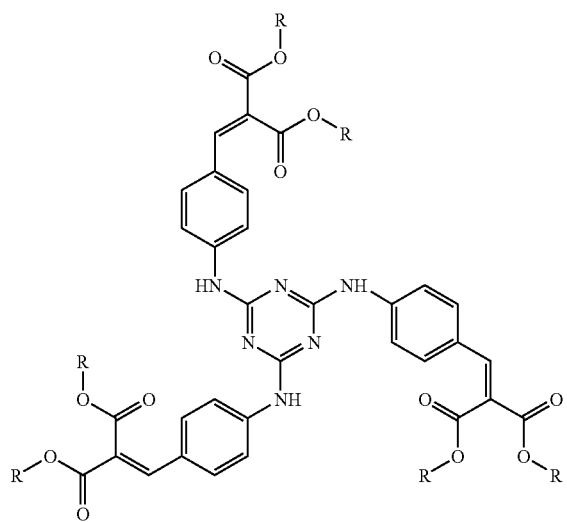

in which the radicals R, which are identical or different, are each a radical of formula (II):

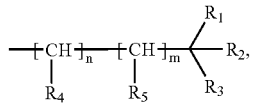

said compound being selected from the group consisting of:

(i) the compounds in which the following conditions are met:

(a) n=m=0; and
  (b) $R_1$, $R_2$, and $R_3$ are each a $C_1$–$C_4$ alkyl radical, or $R_3$ is hydrogen and $R_1$ and $R_2$ together form a $C_5$–$C_8$ ring optionally substituted with one or two $C_1$–$C_4$ alkyl radicals;

(ii) the compounds in which the following conditions are met:

(a) n=1, m is 0 or 1, $R_3$ is hydrogen or a $C_1$–$C_4$ alkyl radical, $R_4$ is a $C_1$–$C_4$ alkyl radical and $R_5$ is hydrogen or a $C_1$–$C_4$ alkyl radical; or n is 0 or 1, m=1, $R_3$ is hydrogen or a $C_1$–$C_4$ alkyl radical, $R_4$ is a $C_1$–$C_4$ alkyl radical and $R_5$ is a $C_1$–$C_4$ alkyl radical; and
  (b) $R_1$ and $R_2$ are each a $C_1$–$C_4$ alkyl radical;

(iii) the compound of formula (1):
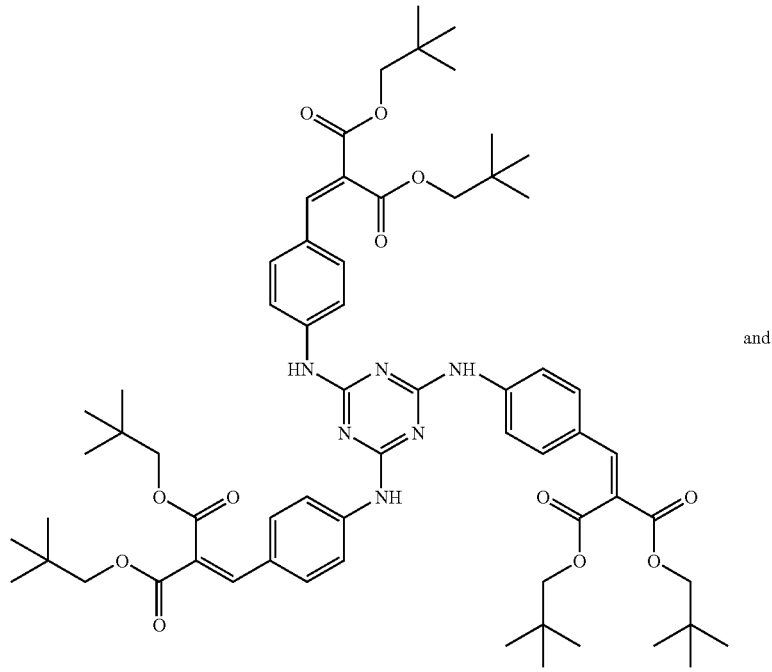
and
(iv) the compound of formula (3):
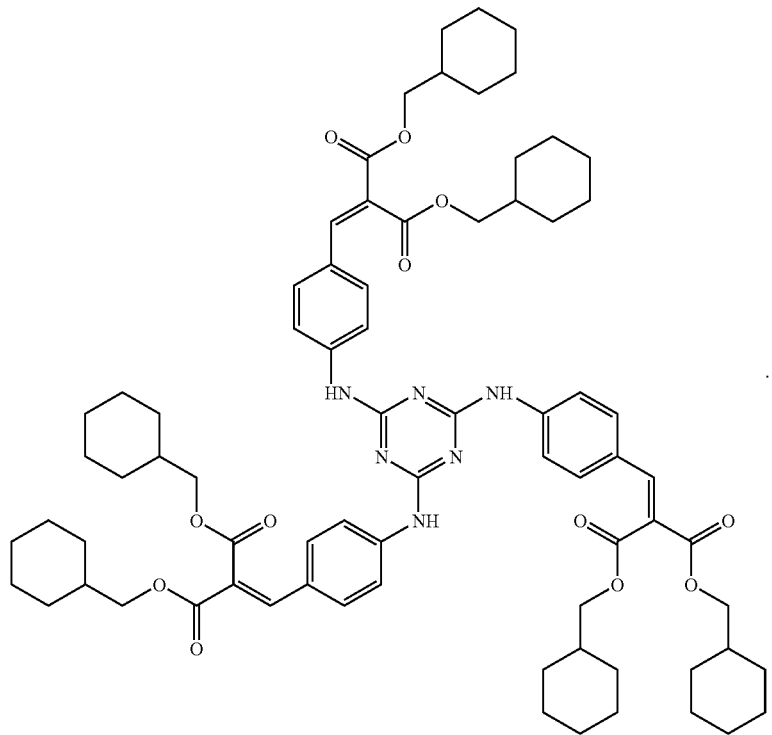

2. A compound as defined by claim 1, selected from the group consisting of:

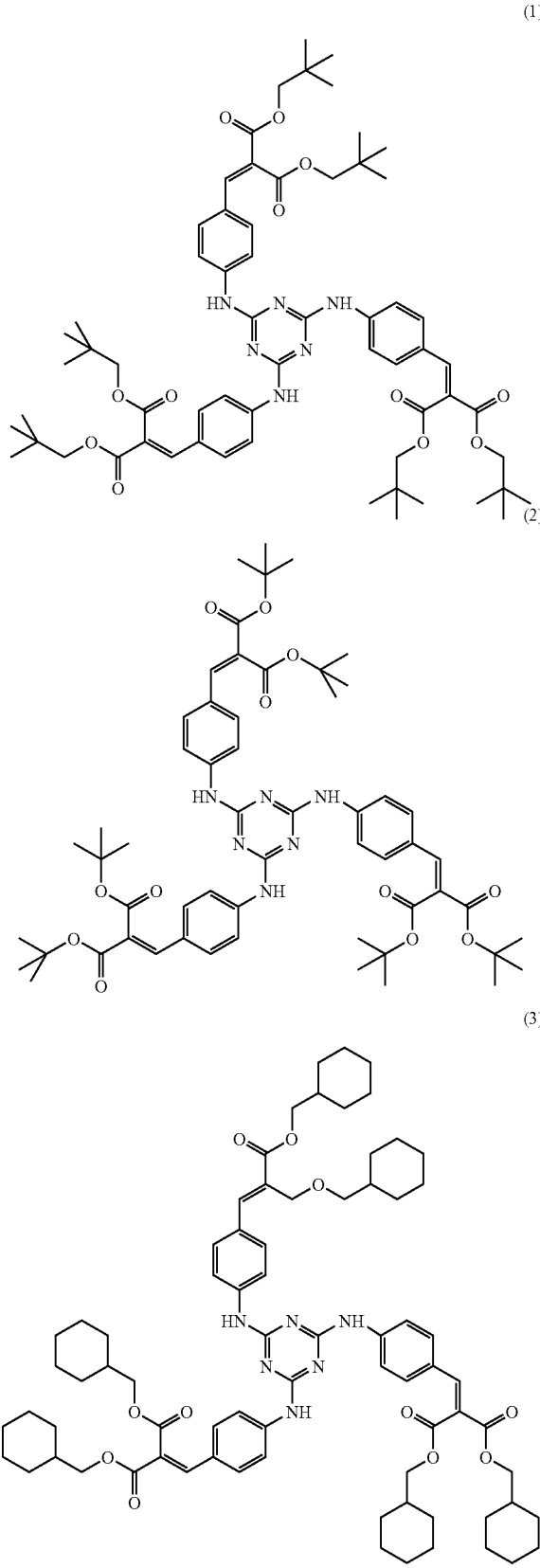

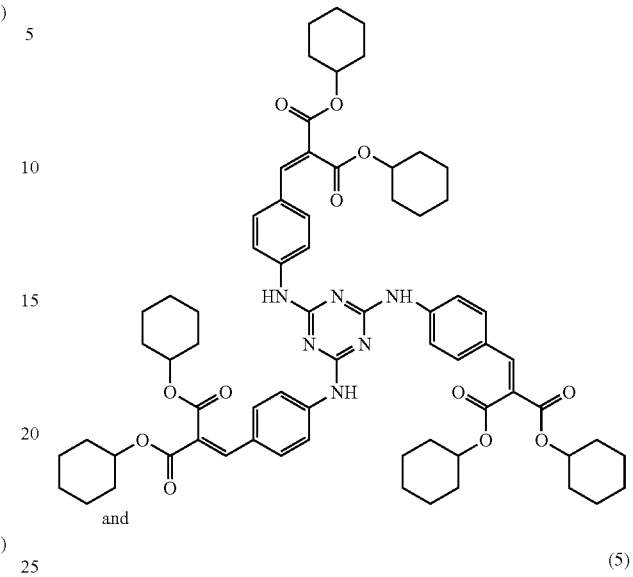

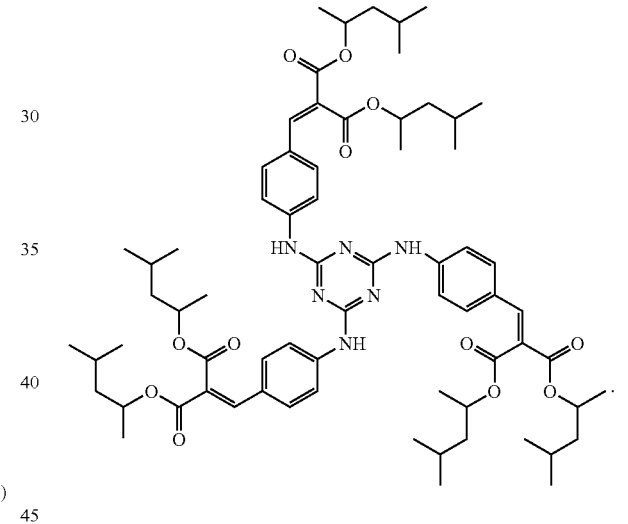

3. A topically applicable cosmetic/dermatological photoprotective composition, comprising an effective UV-photoprotecting amount of one or more compounds of formula (I) as defined by claim 1, formulated into a topically applicable, cosmetically/dermatologically acceptable medium or support therefor.

4. The cosmetic/dermatological composition as defined by claim 3, said one or more compounds of formula (I) comprising from 0.01% to 20% by weight relative to the total weight of the composition.

5. The cosmetic/dermatological composition as defined by claim 3, said one or more compounds of formula (I) comprising from 0.1% to 10% by weight relative to the total weight of the composition.

6. The cosmetic/dermatological composition as defined by claim 3, formulated as an oil-in-water or water-in-oil emulsion.

7. The cosmetic/dermatological composition as defined by claim 3, further comprising one or more additional UV-A-active and/or UV-B-active organic or mineral screening agents.

8. The cosmetic/dermatological composition as defined by claim 7, said one or more additional organic screening agents being selected from the group consisting of the anthranilates; cinnamic derivatives; dibenzoylmethane derivatives; salicylic derivatives; camphor derivatives; triazine derivatives other than those according to the invention; benzophenone derivatives; β,β-diphenylacrylate derivatives; benzotriazole derivatives; benzalmalonate derivatives other than those according to the invention; benzimidazole derivatives; imidazolines; bis-benzoazolyl derivatives; p-aminobenzoic acid (PABA) derivatives; methylenebis(hydroxyphenylbenzotriazole) derivatives; benzoxazole derivatives; screening polymers and screening silicones; dimers derived from α-alkylstyrene; 4,4-diarylbutadienes, and mixtures thereof.

9. The cosmetic/dermatological composition as defined by claim 8, said one or more additional organic screening agent agents being selected from the group consisting of:

Ethylhexyl salicylate,
Ethylhexyl methoxycinnamate,
Butyl methoxydibenzoylmethane,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
2,4,6-Tris(diisobutyl-4'-aminobenzalmalonate)-s-triazine,
Anisotriazine,
Ethyihexyltriazone,
Diethyihexylbutamidotriazone,
Methylenebis(benzotriazolyl)tetramethylbutylphenol,
Drometrizole trisiloxane,
Polysilicone-15,
1,1-Dicarboxy(2,2'-dimethylpropyl)-4,4-diphenylbutadiene,
2,4-Bis[5-1(dimethylpropyl)benzoxazol-2-yl(4-phenyl)imino]-6-(2-ethylhexyl)imino-1,3,5-triazine, and mixtures thereof.

10. The cosmetic/dermatological composition as defined by claim 7, said one or more additional mineral screening agents comprising coated or uncoated metal oxide pigments or nanopigments.

11. The cosmetic/dermatological composition as defined by claim 10, said pigments or nanopigments being selected from the group consisting of coated and uncoated titanium oxide, zinc oxide, iron oxide, zirconium oxide and cerium oxide, and mixtures thereof.

12. The cosmetic/dermatological composition as defined by claim 3, further comprising one or more agents for artificially tanning and/or browning the skin.

13. The cosmetic/dermatological composition as defined by claim 3, further comprising one or more adjuvants selected from the group consisting of fatty substances, organic solvents, ionic thickeners, nonionic thickeners, softeners, humectants, antioxidants, moisturizers, desquamating agents, free-radical scavengers, antipollution agents, antibacterial agents, anti-inflammatory agents, depigmenting agents, propigmenting agents, opacifiers, stabilizers, emollients, silicones, antifoams, insect repellents, fragrances, preservatives, anionic, cationic, nonionic, zwitterionic surfactants, amphoteric surfactants, substance P antagonists, substance CGRP antagonists, fillers, pigments, colorants, polymers, propellants, acidifying agents and basifying agents.

14. The cosmetic/dermatological composition as defined by claim 3, formulated as a nonionic vesicular dispersion, a cream, a milk, a gel, a cream-gel, a suspension, a dispersion, an oil, a powder, a solid, a mousse or a spray.

15. The cosmetic/dermatological composition as defined by claim 3, formulated as a makeup for the eyelashes, the eyebrows, the nails or the skin and in solid or pasty, anhydrous or aqueous form, or in the form of an emulsion, a suspension or a dispersion.

16. The cosmetic/dermatological composition as defined by claim 3, formulated for protecting the hair against ultraviolet rays and in the form of a shampoo, a lotion, a gel, an emulsion or a nonionic vesicular dispersion.

17. A method for photoprotecting a keratinous substrate against the damaging effects of UV-radiation, comprising topically applying thereon a thus effective amount of a topically applicable cosmetic/dermatological composition comprising an effective UV-photoprotecting amount of one or more compounds of formula (I) as defined by claim 1, formulated into a topically applicable, cosmetically/dermatologically acceptable medium or support therefor.

18. A method for controlling the variation in skin color caused by UV-radiation, comprising topically applying to the skin a thus effective amount of a topically applicable cosmetic/dermatological composition comprising an effective UV-photoprotecting amount of one or more compounds of formula (I) as defined by claim 1, formulated into a topically applicable, cosmetically/dermatologically acceptable medium or support therefor.

19. The method as defined by claim 17, said keratinous substrate comprising the skin, lips, scalp and/or hair.

20. The compound as defined by claim 1, having the following-formula:

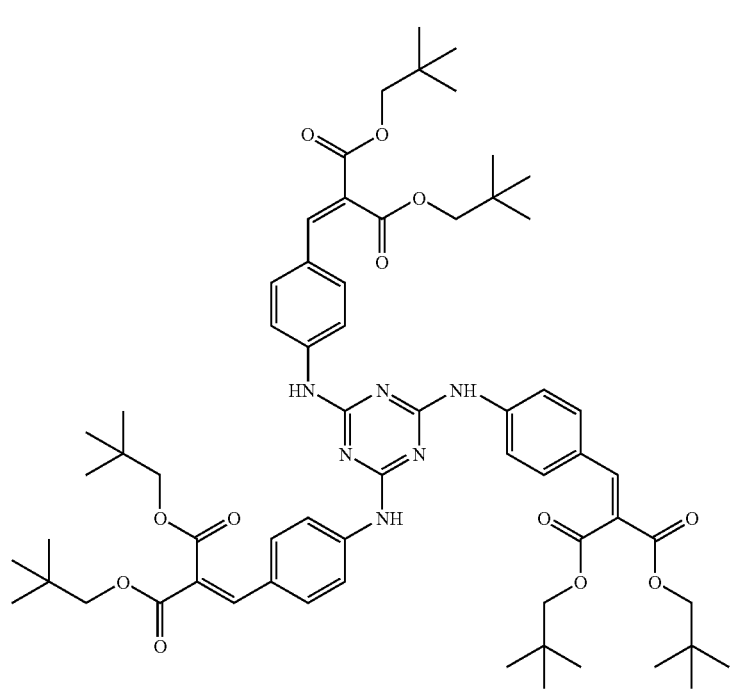
(1)
* * * * *